US012591968B2

(12) United States Patent
Seo et al.

(10) Patent No.: US 12,591,968 B2
(45) Date of Patent: Mar. 31, 2026

(54) ANALYSIS METHOD AND DEVICE FOR CEREBROVASCULAR IMAGE BASED ON CEREBROVASCULAR CHUNK FEATURES

(71) Applicant: SAMSUNG LIFE PUBLIC WELFARE FOUNDATION, Seoul (KR)

(72) Inventors: Woo Keun Seo, Seoul (KR); Yoon Chul Kim, Seoul (KR); Suk Woo Hong, Seoul (KR); Ji Eun Lee, Seoul (KR); Ha Na Song, Seoul (KR); In Young Baek, Seoul (KR); Jong Un Choi, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 329 days.

(21) Appl. No.: 18/321,934

(22) Filed: May 23, 2023

(65) Prior Publication Data

US 2023/0386029 A1    Nov. 30, 2023

(30) Foreign Application Priority Data

May 24, 2022    (KR) ........................ 10-2022-0063692

(51) Int. Cl.
*G06T 7/00*        (2017.01)
*A61B 5/02*        (2006.01)
(52) U.S. Cl.
CPC ........ *G06T 7/0012* (2013.01); *A61B 5/02007* (2013.01); *G06T 2207/30101* (2013.01)

(58) Field of Classification Search
None
See application file for complete search history.

(56)                References Cited

U.S. PATENT DOCUMENTS

2020/0020435 A1*    1/2020    Annavi .................... G06N 3/08

FOREIGN PATENT DOCUMENTS

JP        2008073338 A        4/2008
JP        2020011042 A        1/2020

* cited by examiner

*Primary Examiner* — Leon Flores
(74) *Attorney, Agent, or Firm* — Tarolli, Sundheim, Covell & Tummino LLP

(57)                ABSTRACT

A method of analyzing a cerebrovascular image based on cerebrovascular chunk features is disclosed, the method including receiving, by an analysis device, a cerebrovascular image of a subject; extracting, by the analysis device, a plurality of vascular unit structures from the cerebrovascular image based on geometric features of a 3D model; extracting, by the analysis device, feature values for each of the plurality of vascular unit structures; inputting, by the analysis device, the feature values of each of the plurality of vascular unit structures into a learning model trained in advance, classifying chunks to which each of the plurality of vascular unit structures belongs, and generating chunk features for the cerebrovascular image; and evaluating, by the analysis device, a condition of the subject based on the chunk features.

15 Claims, 11 Drawing Sheets

300 analysis device

500

| storage device (510) | interface device (540) |
| memory (520) | communication device (550) |
| arithmetic device (530) | output device (560) |

ANALYSIS METHOD AND DEVICE FOR CEREBROVASCULAR IMAGE BASED ON CEREBROVASCULAR CHUNK FEATURES

CROSS REFERENCE TO RELAYED APPLICATION

This application claims the benefit under 35 U.S.C. § 119(a) of Korean Patent Application No. 10-2022-0063692, filed on May 24, 2022, in the Korean Intellectual Property Office, the entire disclosure of which is incorporated herein by reference for all purposes.

BACKGROUND

1. Field

The following description relates to a technique for classifying vascular structures based on a new type of vascular unit structure in a cerebrovascular image to identify a subject.

2. Description of the Related Art

Intracranial vascular structures and their variations must be identified for the diagnosis and treatment of cerebrovascular diseases such as brain stroke. Magnetic resonance angiography (MRA) has been widely used to evaluate cerebral artery disease.

There have been previous studies to analyze and quantitatively identify the cerebrovascular structure on the basis of images. In terms of studies in the related art, there were limitations in classifying cerebrovascular structures or identifying mutations only using images, due to the complexity and inter-individual differences in cerebrovascular structures.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a method of analyzing a cerebrovascular image based on cerebrovascular chunk features includes receiving, by an analysis device, a cerebrovascular image of a subject; extracting, by the analysis device, a plurality of vascular unit structures from the cerebrovascular image based on geometric features of a 3D model; extracting, by the analysis device, feature values for each of the plurality of vascular unit structures; inputting, by the analysis device, the feature values of each of the plurality of vascular unit structures into a learning model trained in advance, classifying chunks to which each of the plurality of vascular unit structures belongs, and generating chunk features for the cerebrovascular image; and evaluating, by the analysis device, a condition of the subject based on the chunk features.

In another aspect, there is provided an analysis device for analyzing a cerebrovascular image based on cerebrovascular chunk features includes an input unit receiving a cerebrovascular image of a subject; a storage unit storing a learning model that classifies chunks to which a vascular unit structure belongs; and a computing unit extracting a plurality of vascular unit structures based on geometric features of a 3D model from the cerebrovascular image, inputting feature values for each of the plurality of vascular unit structures into the learning model to classify chunks to which each of the plurality of vascular unit structures belongs and generate chunk features for the cerebrovascular image, and evaluating a condition of the subject based on the chunk features.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

As used herein, the term "and/or" includes any one and any combination of any two or more of the associated listed items.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Hereinafter, the technology of analyzing a cerebral artery MRA image and classifying a vascular structure in units of certain cerebrovascular unit structure (chunk) will be described.

The researcher has analyzed the image using time-of-flight (TOF) MRA. Therefore, the following description is described based on TOF MRA. The technology described below may also be applied to other types of medical images.

Herein, it is noted that the analysis device analyzes the TOF MRA to classify the cerebral artery chunks. The analysis device may be implemented with various devices capable of constant data processing. For example, the analysis device may be implemented as a PC, a server on a network, a smart device, a chipset with embedded dedicated program, and the like.

Figure 1:
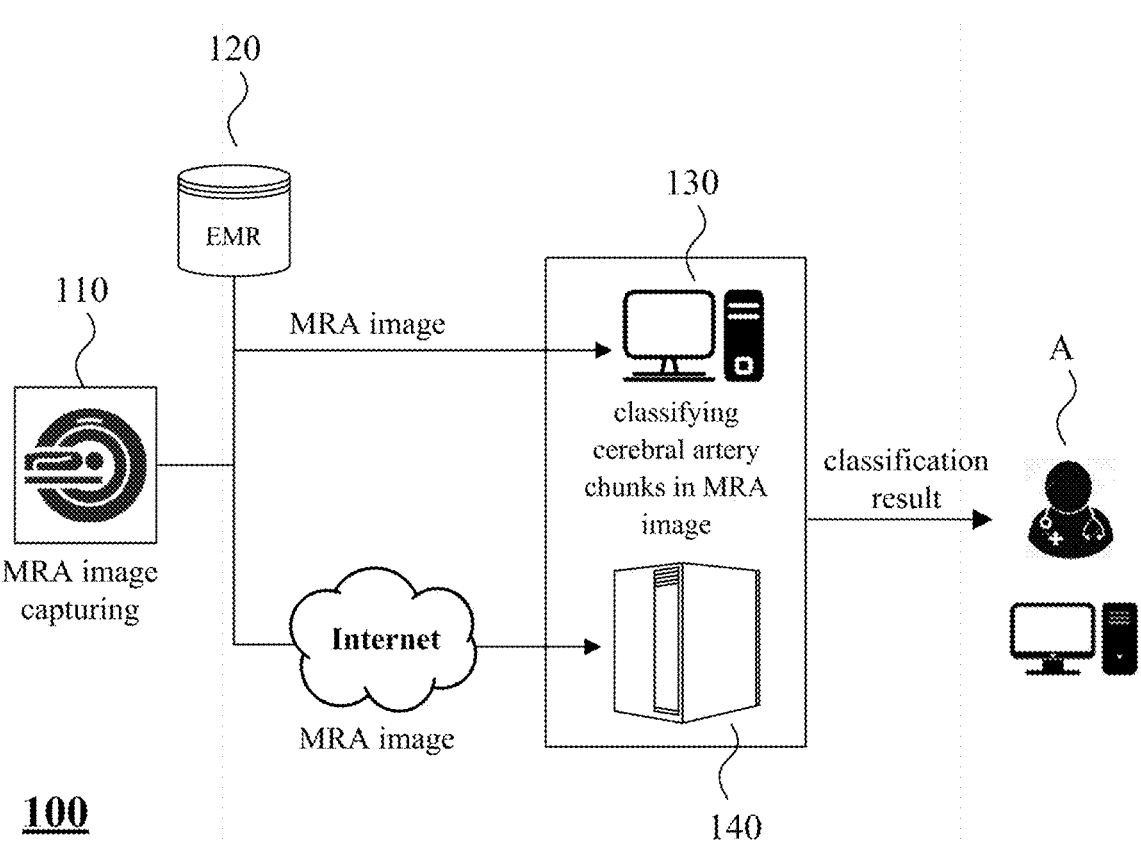
FIG. 1 illustrates an example of system for classifying cerebral artery chunks.

FIG. 1 illustrates an example of a system 100 for classifying cerebral artery chunks. In FIG. 1, an analysis device may be implemented as a computer terminal 130 and a server 140.

A magnetic resonance angiography (MRA) 110 generates an MRA image of a patient. An MRA image or TOF MRA image generated by the MRA 110 may be stored in an electronic medical record (EMR) 120 or a separate database.

In FIG. 1, a user A may classify cerebral artery chunks in an MRA image using a computer terminal 130. The computer terminal 130 may receive the MRA image from the MRA 110 or the EMR 120 through a wired or wireless network. In some cases, the computer terminal 130 may be physically connected to the MRA 110. The computer terminal 130 may extract a certain cerebrovascular structure from the MRA image, and input features of the extracted cerebrovascular structure into a learning model built in advance, to derive a classification result of the cerebral artery chunks. A detailed classification process of the cerebral artery chunks will be described later. The user A may check the classification result from the computer terminal 130. The user A may evaluate a clinical condition of the current subject based on the classification result of the subject. For example, the user A may evaluate the subject as a normal condition group, an abnormal condition group, or a disease risk group.

The server 140 may receive the MRA image from the MRA 110 or the EMR 120. The server 140 may extract a certain cerebrovascular structure from the MRA image, and input features of the extracted cerebrovascular structure into a learning model built in advance, to derive a classification result of the cerebral artery chunks. A detailed classification process of the cerebral artery chunks will be specifically described later. The server 140 may transmit the classification result of the cerebral artery chunks to the user A. The user A may check the classification result through his terminal. The user A may evaluate a clinical condition of the current subject based on the classification result of the subject. For example, the user A may evaluate the subject as a normal condition group, an abnormal condition group, or a disease risk group.

The computer terminal 130 and/or the server 140 may store the classification result in the EMR 120.

Figure 2:
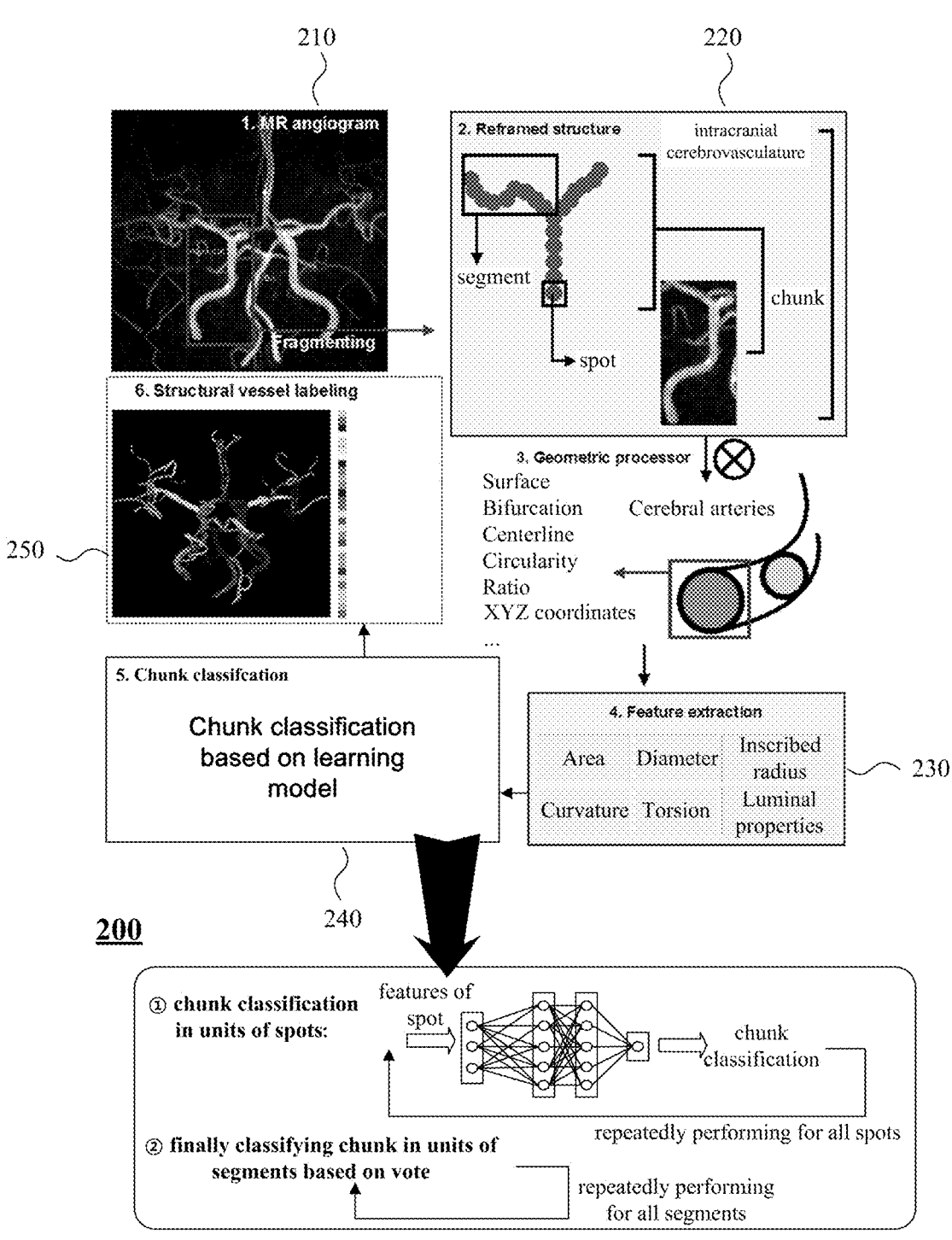
FIG. 2 illustrates an example of process of classifying cerebral artery chunks.

FIG. 2 illustrates an example of a process 200 for classifying cerebral artery chunks. With regard to FIG. 2, a procedure in which the researcher extracts vascular structures from the TOF MRA image and classifies vessel chunks based on features of the vascular structures will be described. In addition, with regard to FIG. 2, an image processing procedure and a model-building procedure performed by the researcher will also be described.

The analysis device receives the TOF MRA image (210). The analysis device processes a structure to extract image features from the TOF MRA image (220). The analysis device may detect a desired vascular structure using geometric processing that reconstructs a 3D model.

The vascular structure refers to a spot, segment, chunk, and branch. The analysis device extracts the vascular structure from the input image using a certain image processing program, to obtain features of the corresponding structure.

First, the vasculature system used by the researcher will be described. The researcher has configured the vascular unit structure at four hierarchical levels, which is different from the method used in the clinical neurology field in the related art.

A spot refers to a basic unit of a 3D cerebral artery tree cubic cell with a regular spacing (size) from the artery centerline. The researcher has defined the spot as a cubic cell with a spacing of 0.2801 mm from the arterial centerline.

A segment is composed of a plurality of spots which are segmented based on a bifurcation point in the vascular structure. That is, the segment corresponds to a set of consecutive spots between branch points of blood vessels.

The vessel branch is composed of a plurality of segments. The vessel branch may be identified as one of specific types on a segment-by-segment basis according to the geometry of a vascular bifurcation point. The researcher has classified the vessel branch into 62 types of branches according to the geometry of the vascular bifurcation point. In other words, the vessel branch may be regularly classified according to the vascular unit structure proposed by the researcher. Meanwhile, the vessel branch may be identified by nomenclature traditionally used in the clinical field.

The vessel branch may be segmented into (i) symmetry, (ii) anterior or posterior, (iii) basal or pial, and (iv) middle cerebral artery cerebral arteries (MCA), anterior cerebral arteries (ACA), or posterior cerebral arteries (PCA), according to clinical criteria. Based on such segmentation, the researcher has defined a chunk as a higher structure than the branch. The chunk may be classified using at least one criterion among groups including (i) symmetry, (ii) anterior or posterior, (iii) basal or pial, and (iv) middle cerebral arteries (MCA), anterior cerebral arteries including criteria for the anterior cerebral arteries (ACA) and posterior cerebral arteries (PCA). In other words, the chunk clinically refers to vessel branches of a higher mass.

The researchers have defined 20 types of vascular chunks as shown in Table 1 below. Each chunk may be further subdivided into one or more branches.

TABLE 1

| number | chunk (abbreviation) | Chunk code |
|---|---|---|
| 1 | Anterior communicating artery (ACOA) | A0 |
| 2 | Right internal carotid artery (RtICA) | A1 |
| 3 | Left internal carotid artery (LtICA) | A2 |

TABLE 1-continued

| number | chunk (abbreviation) | Chunk code |
| --- | --- | --- |
| 4 | Right anterior cerebral basal arteries - middle cerebral artery (RtBasalMCA) | A3 |
| 5 | Left anterior cerebral basal arteries - middle cerebral artery (LtBasalMCA) | A4 |
| 6 | Right anterior cerebral basal arteries - anterior cerebral artery (RtBasalACA) | A5 |
| 7 | Left anterior cerebral basal arteries - anterior cerebral artery (LtBasalACA) | A6 |
| 8 | Right anterior cerebral pial arteries - middle cerebral artery (RtPialMCA) | A7 |
| 9 | Left anterior cerebral pial arteries - middle cerebral artery (LtPialMCA) | A8 |
| 10 | Right anterior cerebral pial arteries - anterior cerebral artery (RtPialACA) | A9 |
| 11 | Left anterior cerebral pial arteries - anterior cerebral artery (LtPialACA) | A10 |
| 12 | Right posterior - vertebral artery (RtVA) | P1 |
| 13 | Left posterior - vertebral artery (LtVA) | P2 |
| 14 | Right posterior basal - posterior cerebral artery (RtBasalPCA) | P3 |
| 15 | Left posterior basal - posterior cerebral artery (LtBasalPCA) | P4 |
| 16 | Right posterior pial - posterior cerebral artery (RtPialPCA) | P5 |
| 17 | Left posterior pial - posterior cerebral artery (LtPialPCA) | P6 |
| 18 | Right posterior - superior cerebral artery, anterior inferior cerebral artery, posterior inferiorcerebellar artery (RtCbll) | P7 |
| 19 | Left posterior - superior cerebral artery, anterior inferior cerebral artery, posterior inferiorcerebellar artery (LtCbll) | P8 |
| 20 | Basilar artery (BA) | P0 |

The researcher has performed an isosurface dissection to create a vascular surface model using the vascular modeling toolkit (VMTK) library. The researcher has removed artifacts using bicubic interpolation and resampled the rough image on a regular flat grid. This enables a z-axis voxel to be fitted to an isovoxel image scale. A contiguous 3D space may be divided into a number of cells based on each vertex of the isosurfaces. Through this process, the researcher may extract the main arterial centerline from the border surface of each cell in the cerebrovascular MRA image.

The analysis device may segment a vascular surface into cells of a certain size in the cerebrovascular MRA image, and extract the skeleton and the starting point of the centerline in the brain artery based on the vascular surface.

The analysis device may perform refinement on the vascular skeleton to make the end point of the centerline more distinct. The analysis device may (i) skeletonize the cerebrovascular region and surface, (ii) prune branches under a predetermined threshold, (iii) create a linked list of tree structures based on the refined scaffold structure, and (iv) determine the end point by specifying a leaf node from the linked list. The analysis device may extract the centerline of the blood vessel by tracing the cell boundary connecting the determined start point and end point.

Thereafter, the analysis device quantifies the vascular feature vectors for groups separated based on the divergence point of the center line (230). The quantified vascular features include cerebral vessel cross-sectional area, maximally inscribed sphere radius, minimum and maximum diameters, maximum-minimum radius ratio, surface circumference, distortion, curvature, and luminal circularity.

The researcher has performed automated segmentation according to normal nomenclature rules of the cerebrovascular system in the brain MRA image, and built a model to perform classification (labeling) for the cerebral artery chunks. Here, the analysis device classifies the vascular structure at a chunk level using a learning model built in advance (240). Furthermore, in some cases, the analysis device may classify whether spots belonging to the chunk belong to a specific branch in units of spots.

As learning models for classifying cerebral artery chunks, various models may be used. Here, the machine learning model includes a decision tree, a random forest (RF), a K-nearest neighbor (KNN), a Naive Bayes, a support vector machine (SVM), and an artificial neural network (ANN). Herein, the ANNs are statistical learning algorithms that imitate biological neural networks. Various neural network models are being studied. A deep learning network (DNN) may model complex non-linear relationships like a general artificial neural network. The DNN have been studied as various types of models, such as, for example, convolutional neural networks (CNNs), recurrent neural networks (RNNs), restricted Boltzmann machines (RBMs), deep belief networks (DBNs), generative adversarial networks (GANs), relation networks (RLs), and the like.

The analysis device first inputs feature vectors of each spot into the learning model in units of spots extracted from the TOF MRA image. Here, the feature vectors of the spot may be values for at least one of the vascular features as described above. Furthermore, the feature vector of the spot may further include a brightness of the spot region.

The researcher has used DNN as the learning model. The learning model classifies input spots at a chunk level. Meanwhile, the learning model may be a voting-based ensemble model using heterogeneous learning models. This process is repeated for all spots. As a result, the analysis device obtains a result of chunk classification for all spots.

Furthermore, the analysis device may finish the chunk classification for all spots, and then perform voting-based classification for accuracy improvement (secondary classification). To this end, the analysis device distinguishes the segments based on the bifurcation points of blood vessels. This process enables the analysis device to distinguish segments of the entire blood vessel. The analysis device may perform chunk allocation based on a majority vote in units of segments. The analysis device may check the result of classification by the learning model for each of the spots belonging to the same segment, and determine the most classified result (chunk type) as a final classification result of spots constituting the corresponding segment. This enables the analysis device to classify the chunk to which the corresponding segment (or spots belonging to the corresponding segment) belongs in units of segments. This process is repeated for all segments.

The analysis device may compute information obtained by performing classification in units of cerebral artery chunks in the brain MRA image of the subject (patient) through the process shown in FIG. 2 (250). The medical staff may diagnose a clinical condition for the subject based on the final classification result.

Figure 3:
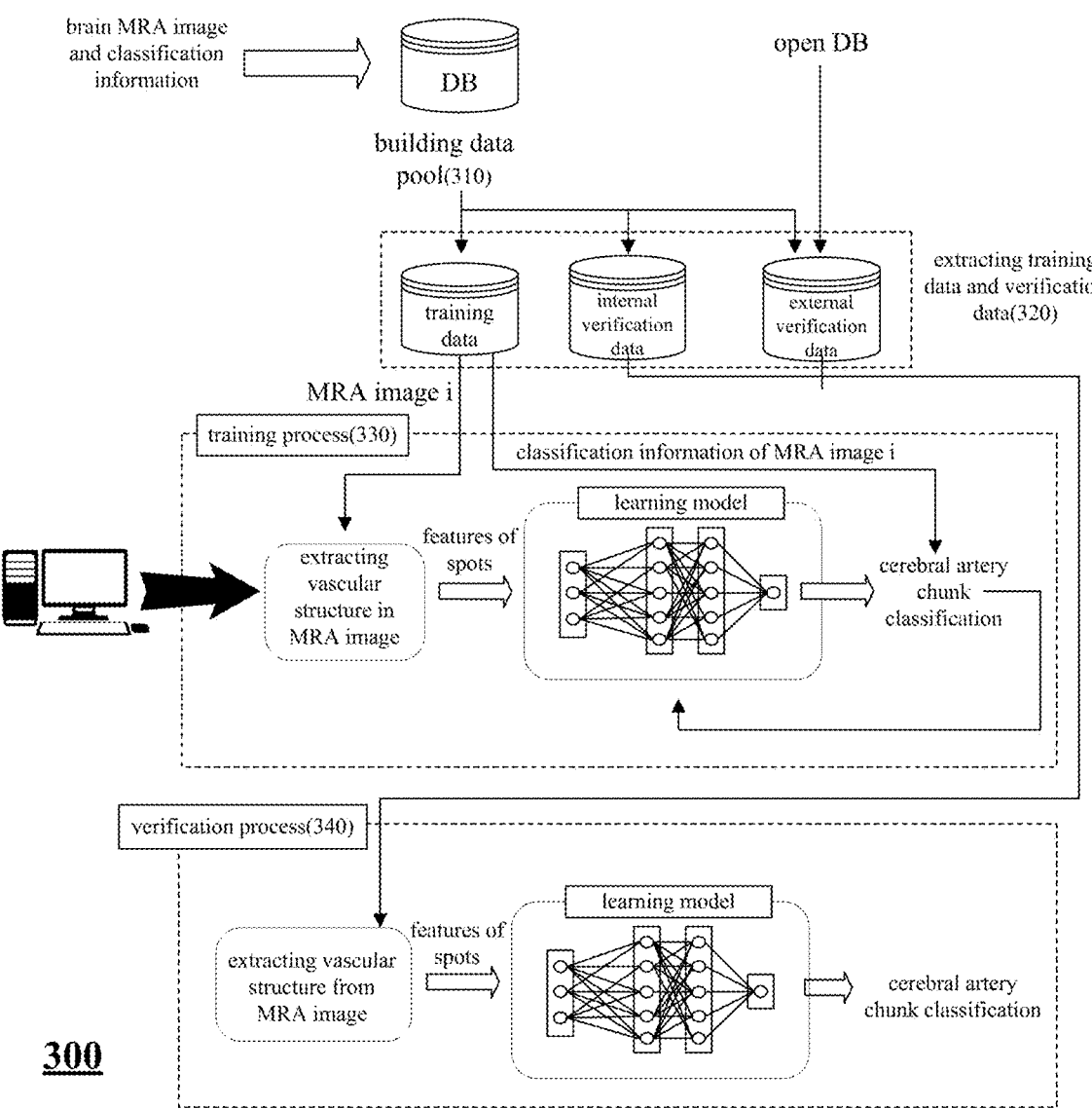
FIG. 3 illustrates an example of training and verification process for a model used for classifying cerebral artery chunks.

FIG. 3 illustrates an example of a training and verification process 300 for a model used for classifying cerebral artery chunks.

The researcher studied stroke patients clinically confirmed at Samsung Medical Center after obtaining consent from them. The control cohort is defined as normal people who have undergone MRA imaging from Jan. 1, 2013 to Dec. 31, 2016 at the Samsung Hospital Health Examination Center.

The researcher studied a healthy control group, stroke patients with intracranial atheroscledrosis (ICAS) (stroke with ICAS, ICAS group), and normal stroke patients (stroke group). The researcher studied 157 participants between the ages of 20 and 94. A total of 157 participants were divided into the control group with 42 people, the ICAS group with 46 people, and the stroke group with 69 people. The researcher used 70% of the collected cohort data as training data and 30% as validation data.

The researcher has analyzed the TOF MRA of the participants to identify the structure of the cerebral artery vessels in advance (discriminating the images using experts). That is, the researcher classified the cerebral artery chunks in the training data and verification data in advance. The classification information for the cerebral artery chunks is simply referred to as classification information hereinafter.

The researcher builds a data pool for training and verification (310). The data pool contains brain MRA images of the participants.

The researcher extracts training data and verification data (320). The researcher prepares the training data and the internal verification data based on the MRA images acquired through the affiliated institution. The training data and the verification data each include a brain MRA image of a specific subject and classification information for the image. In addition, the researcher may perform external verification using images prepared by the corresponding institution. Of course, the external verification data may be prepared by collecting MRA images and classification information in an external open database (DB).

The researcher trains the aforementioned learning model using training data (330). The learning model is trained on an analysis device or a separate computer device. Hereinafter, a device for building the learning model is referred to as a learning device. The learning device trains the learning model using the training data. The learning device extracts the aforementioned vascular unit structures from the MRA image. The process of extracting the vascular unit structure is the same as described above. The vascular unit structures include spot, segment, and the like, as described above. The learning device classifies chunks to which the corresponding spot belongs by inputting features in units of spots in the extracted vascular unit structures into the learning model. In this process, the learning device inputs features of the spots into the learning model, and then compares a probability value of chunk classification output by the learning model with classification information on the corresponding spot to update parameters of the learning model. FIG. 3 illustrates a learning process performed using MRA image i, in which the learning process is repeatedly performed using various training data. By repeating this process, the learning model is trained in such a manner as to output the chunk classification of the corresponding spot based on features of the input spots.

Meanwhile, even in the training process of the learning model, the learning device performs voting based on the classification results of spots belonging to each segment, to determine a final classification result of spots belonging to the corresponding segment.

Then, the learning device may verify the learning model trained using internal verification data and/or external verification data (340). The learning device extracts the vascular unit structure from the input MRA image, and inputs features of each spot into the learning model, to classify chunks to which the corresponding spots belong. The researcher confirmed the performance of the classification result using verification data.

Figure 4:
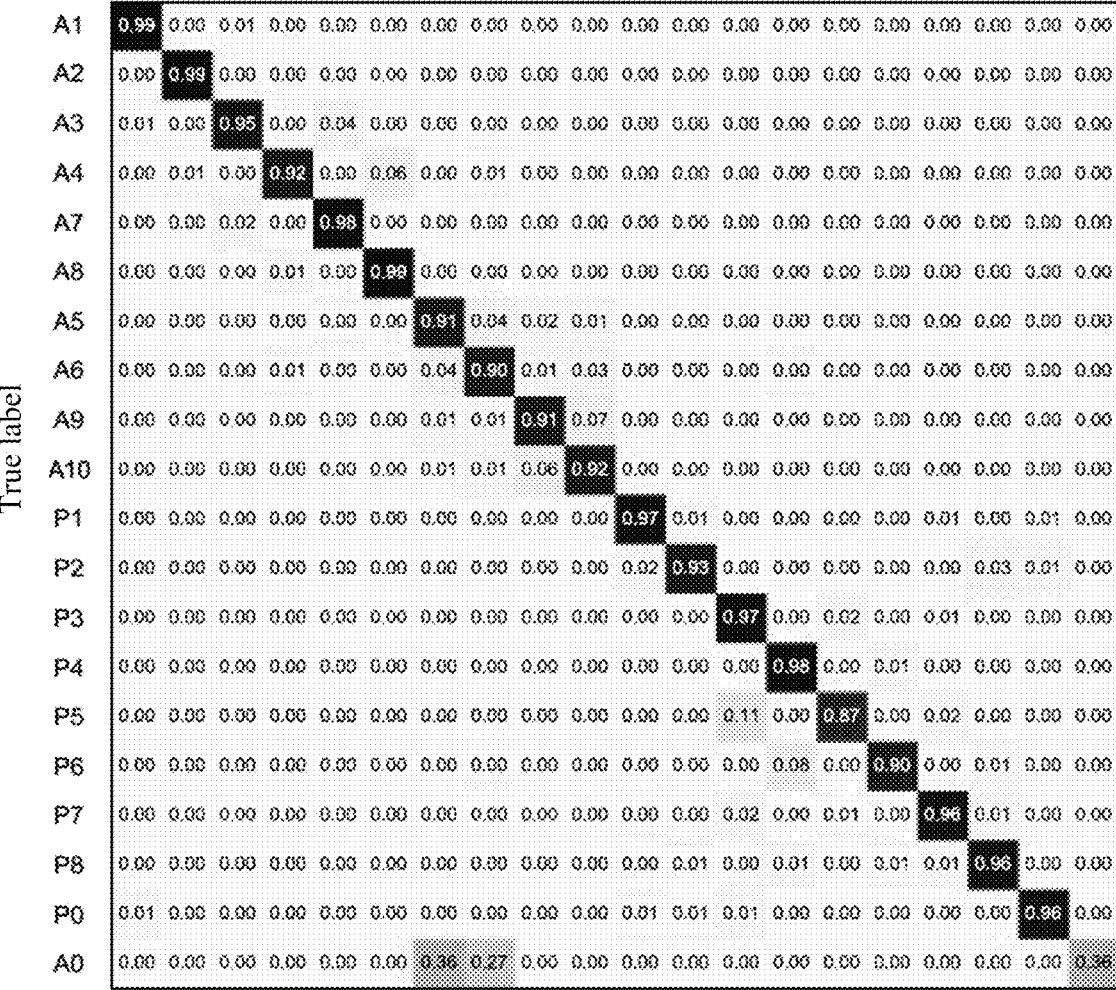
FIG. 4 illustrates a result of predicting chunks for a healthy control group.
Figure 5:
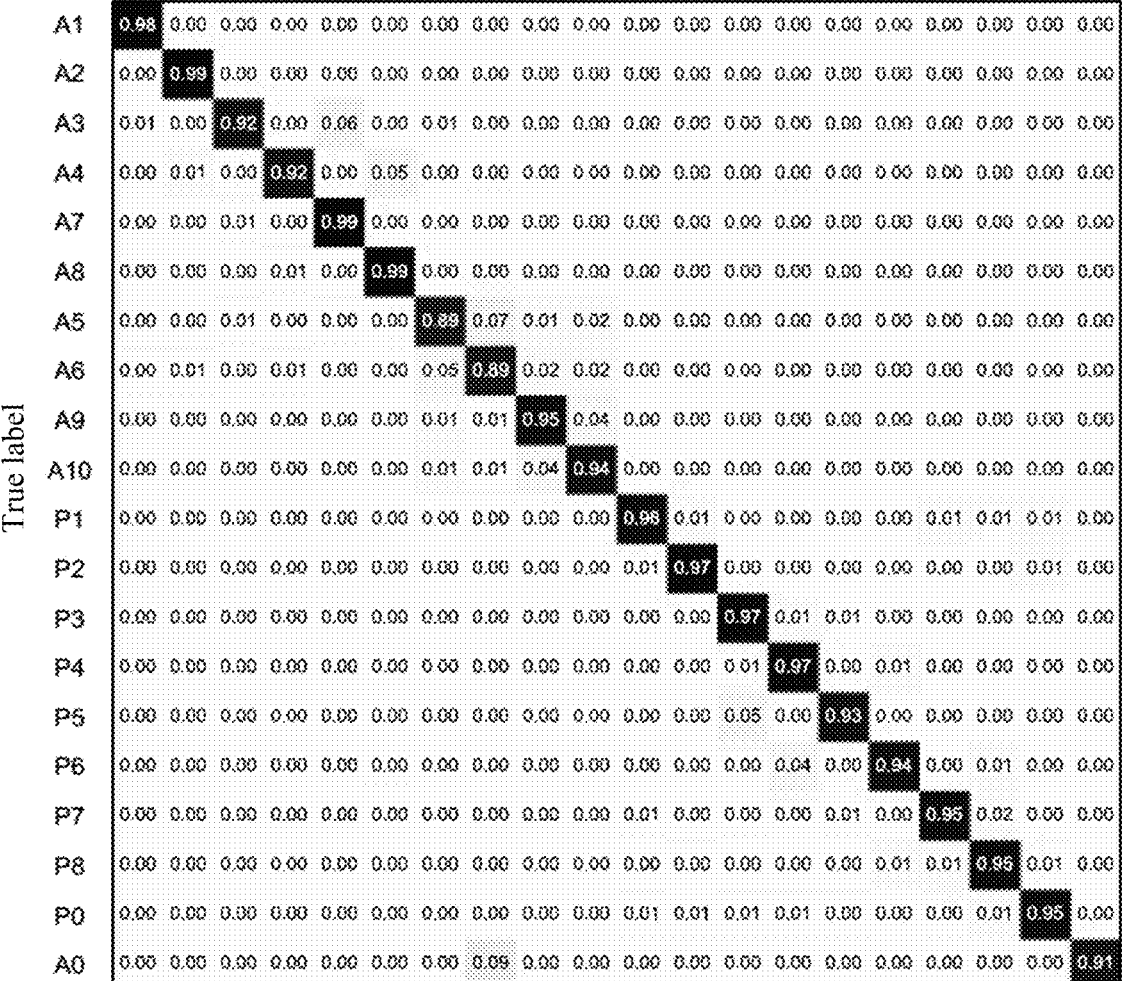
FIG. 5 illustrates a result of predicting chunks for an ICAS group.
Figure 6:
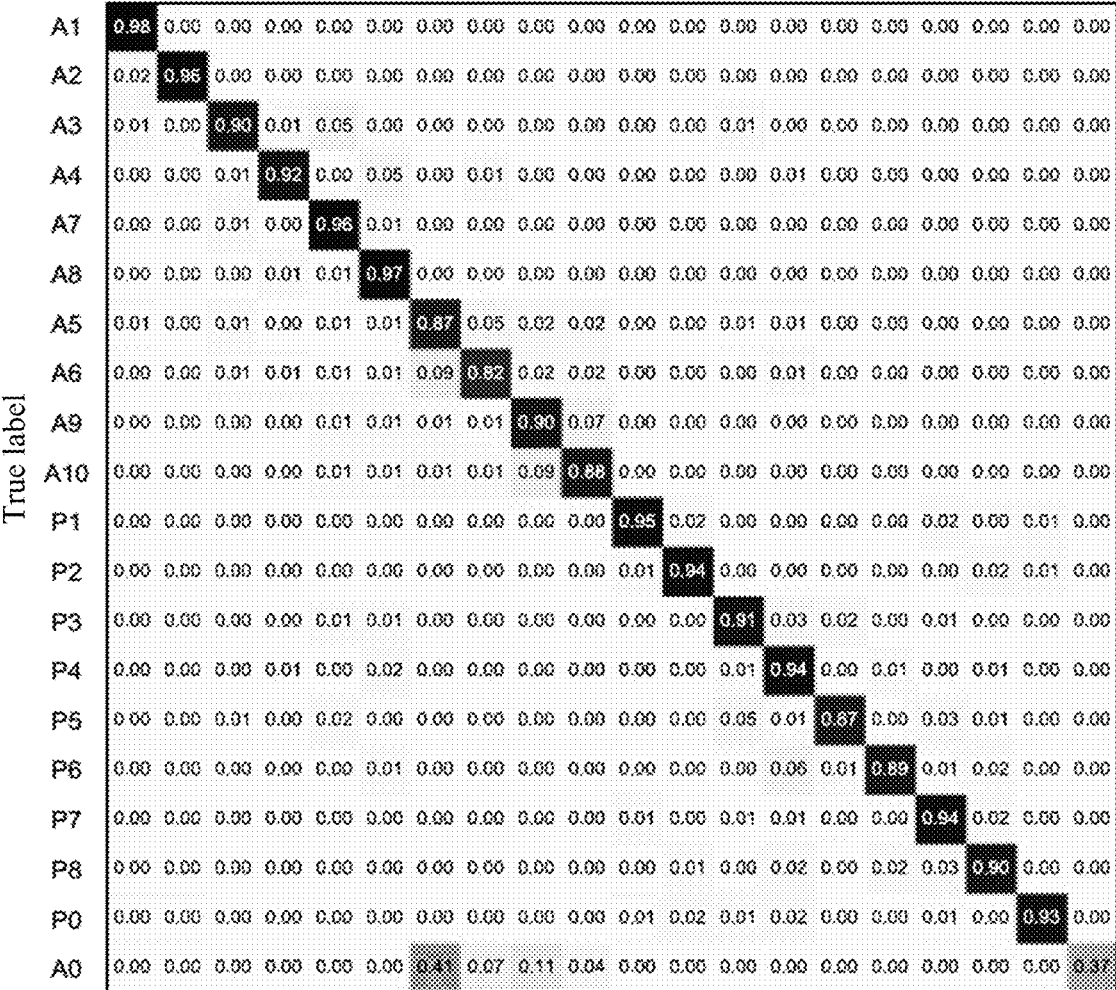
FIG. 6 illustrates a result of predicting chunks for a stroke group.

FIGS. 4 to 6 illustrate results of verifying the prediction performance for chunks in the cerebrovascular structure.

FIG. 4 illustrates a result of predicting chunks for the healthy control group. FIG. 5 illustrates a result of predicting chunks for the ICAS group. FIG. 6 illustrates a result of predicting chunks for the stroke group. In the graphs of FIGS. 4 to 6, the vertical axis indicates a true label, and the horizontal axis indicates a predicted label by the model. In the model built by the researcher, among 20 chunks, only the left anterior basolateral anterior cerebral artery chunks (left anterior basal ACA, LtBasalACA, A6) showed 82% prediction accuracy, and the rest showed prediction accuracy between 87% and 99%. In addition, the model built by the researchers showed similar prediction accuracy for each chunk in the healthy control group, the stroke group, and the ICAS group. However, the anterior communicating artery (ACOA, A0) showed some predictive deviation depending on the subject group. This may be due to the limited sample size and high anatomical variability for ACOA. AUC (area under the curve)-ROC (receiver operating characteristic) for chunk classification showed high performance overall, ranging from 0.99 to 1.00, and the precision-recall curve (PRC) showed 0.992.

The researcher has evaluated whether different subject groups could be classified based on cerebral artery chunks. That is, the researcher has evaluated whether different subject groups may be identified from each other based on types of chunks. To this end, the researcher reduced the dimensions of chunks of each subject group using UMAP and performed clustering in a plane space. The reduction of the dimensions allows to maintain the global data structure, since it has non-linear characteristics.

Figure 7:
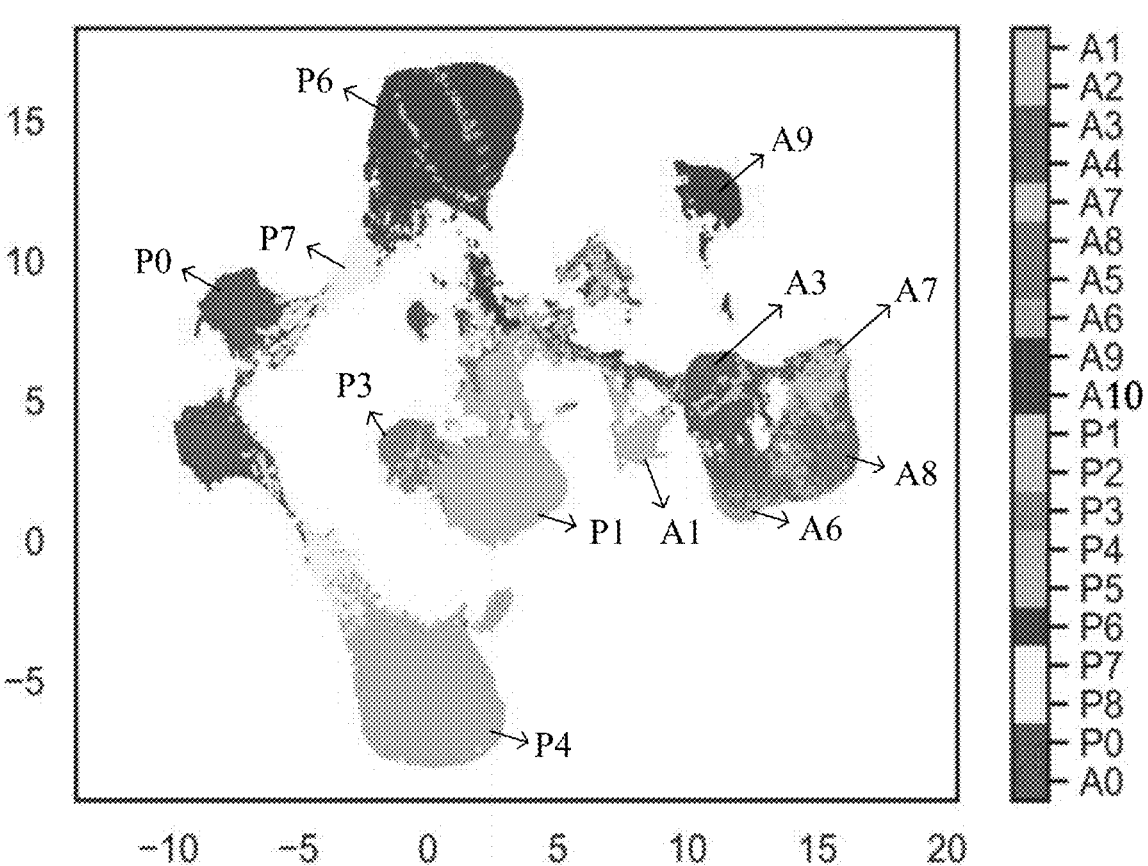
FIG. 7 illustrates a result of clustering based on a type of chunk for the control group (normal person).
Figure 8:
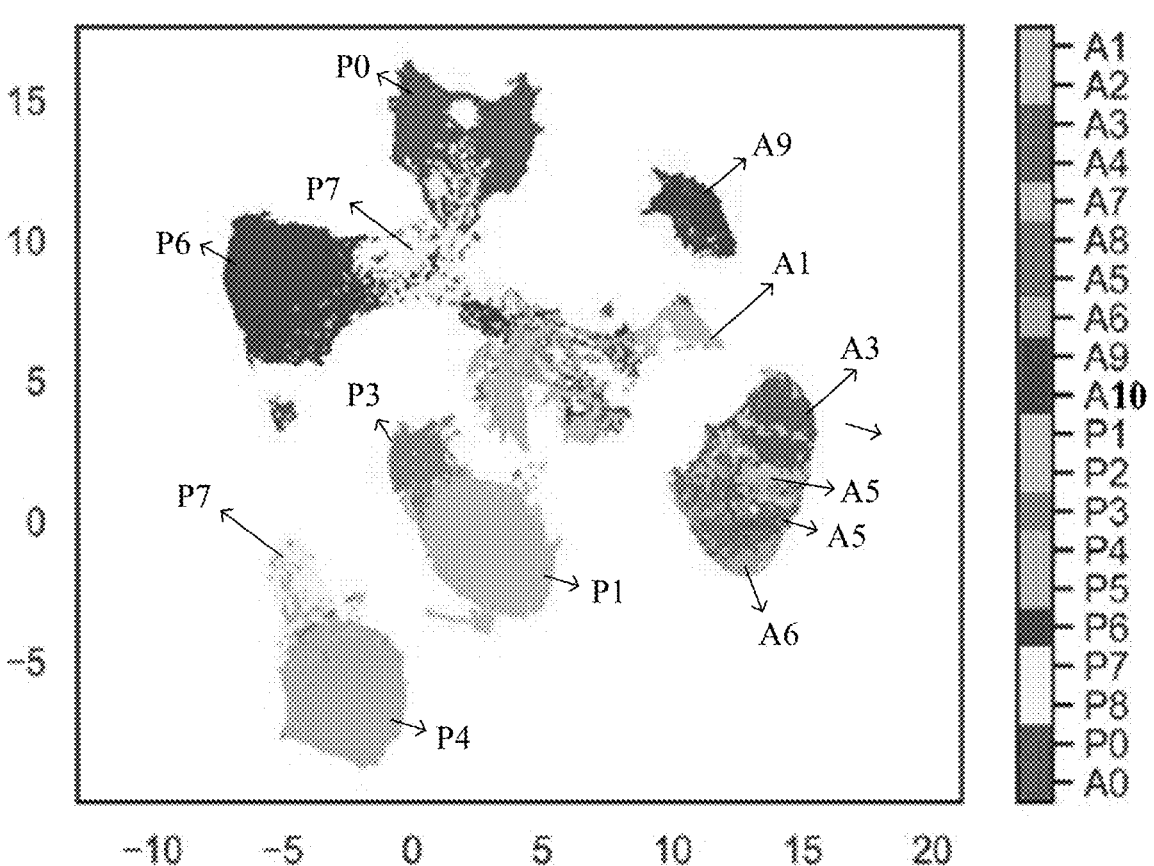
FIG. 8 illustrates a result of clustering based on a type of chunk for the stroke group.
Figure 9:
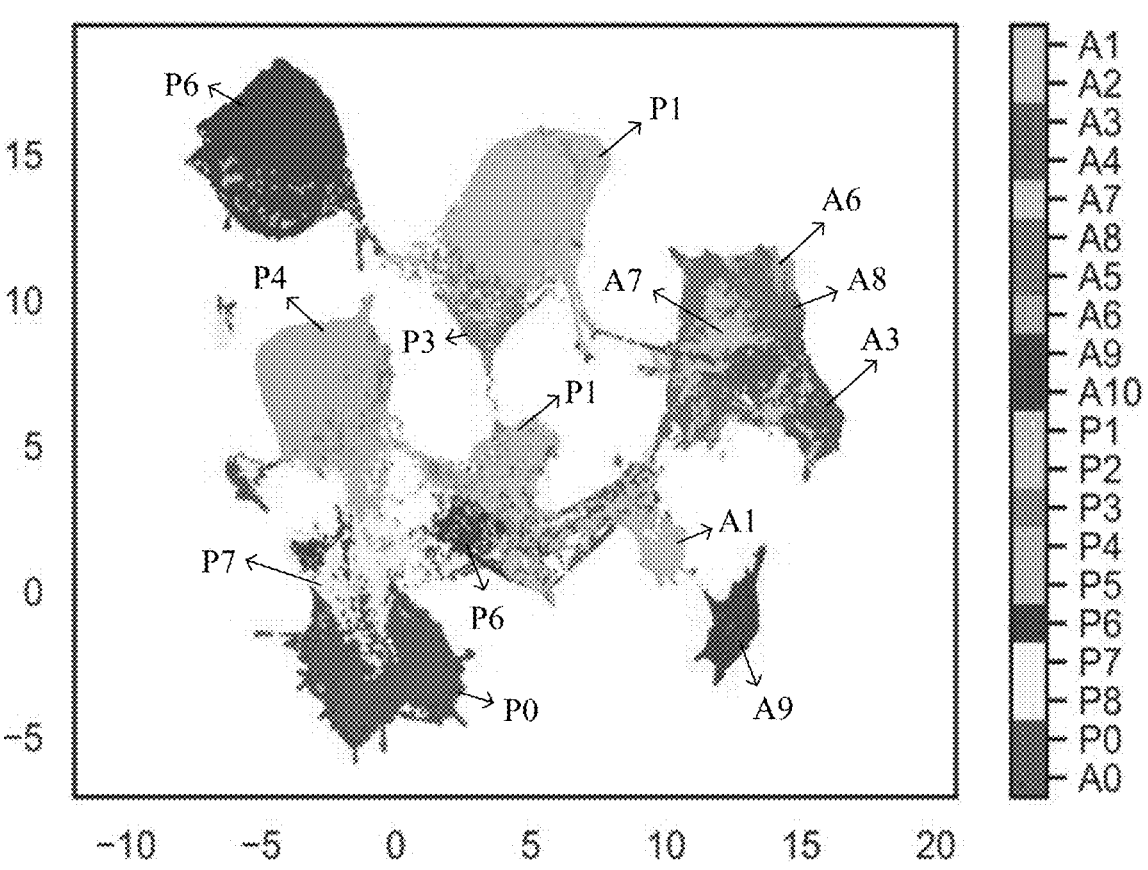
FIG. 9 illustrates a result of clustering based on a type of chunk for the ICAS group.

FIGS. 7 to 9 illustrate clustering results based on types of chunks for different groups. FIGS. 7 to 9 illustrate 20 chunks in different level (strength) of shade. FIG. 7 illustrates a result of clustering based on a type of chunk for a control group (normal person). FIG. 8 illustrates a result of clustering based on a type of chunk for a stroke group. FIG. 9 illustrates a result of clustering based on a type of chunk for an ICAS group. Referring to FIGS. 7 to 9, the control group (normal person), the stroke group, and stroke group with ICAS show clustering characteristics different from each other. Therefore, when classifying the types of cerebral artery chunks, the analysis device may distinguish between normal persons and stroke patients. Furthermore, the analysis device may classify patients into groups with different phenotypes, such as general stroke patients and stroke patients with ICAS.

Figure 10:
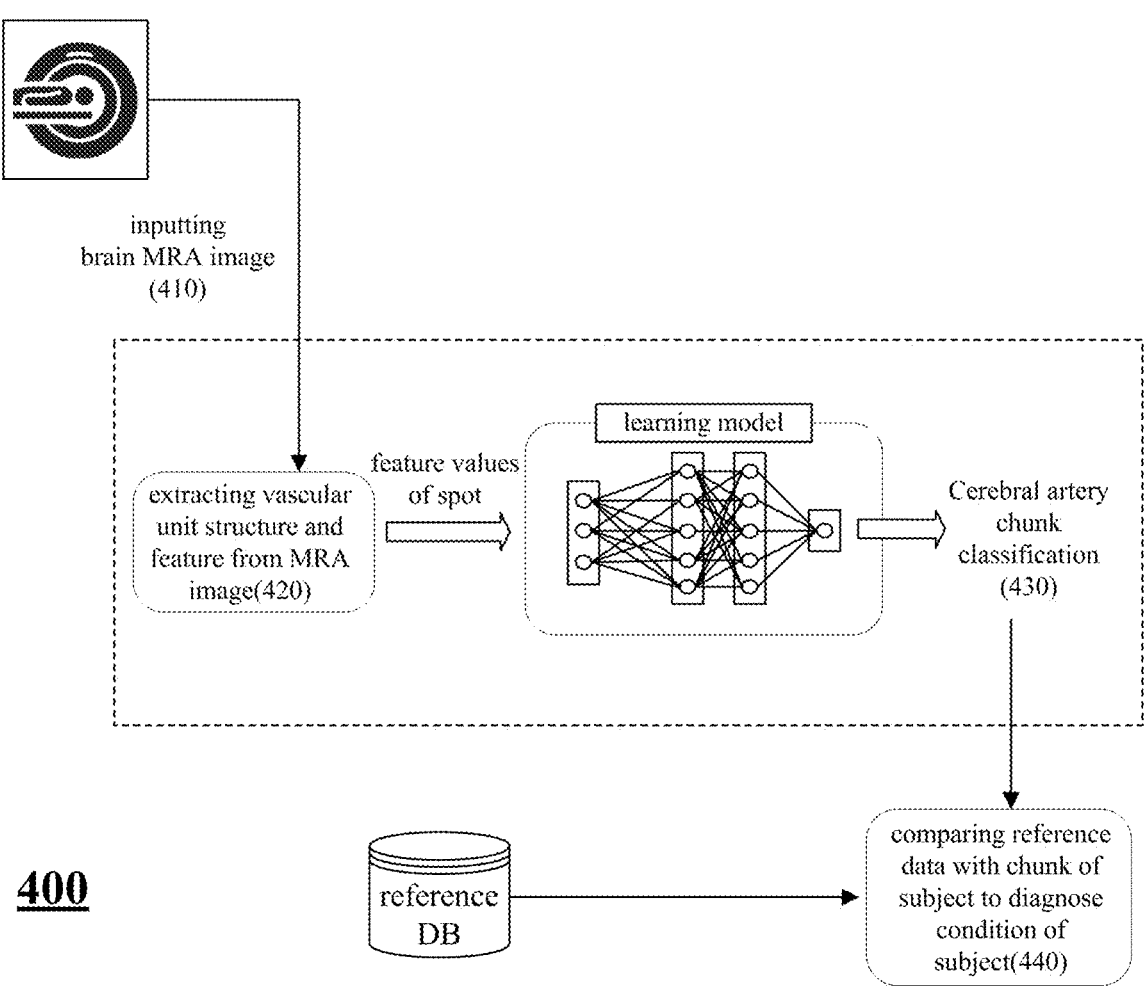
FIG. 10 illustrates an example of a process of diagnosing a condition of the subject by classifying cerebral artery chunks.

FIG. 10 illustrates an example of a process 400 of diagnosing a condition of the subject by classifying cerebral artery chunks.

The analysis device receives a brain MRA image of the subject (410).

The analysis device extracts vascular unit structures from the brain MRA image, and extracts feature values for the vascular unit structures (420). The process of extracting vascular unit structures is as described above. The vascular unit structures include spots, segments, and the like, as described above.

The analysis device inputs features in units of spots in the extracted vessel unit structure into the learning model, and classifies cerebral artery chunks (430). The analysis device may classify the cerebral artery chunks for all the spots. This enables the analysis device to obtain information on the type of cerebral artery chunk of the subject.

Thereafter, the analysis device may compare the reference data with the information on the type of cerebral artery chunk of the subject, to diagnose the condition of the subject (440).

The information on the type of chunk may include a list of types of chunks possessed by the subject, information generated by performing clustering for the types of chunks, and certain information computed by inputting the chunk types into a deep learning model trained in advance. Since the information on the type of chunk may have a certain pattern according to phenotypes, it may be referred to as a chunk pattern or a chunk feature.

The reference data refers to information on types of cerebral artery chunks (chunk pattern) that are prepared in advance for various phenotypes. For example, the reference data may include chunk type information of a normal person, chunk type information of a specific disease, chunk type information of a specific phenotype, and the like.

It is assumed that the reference data has chunk type information of normal persons, chunk type information of stroke patients with ICAS, and chunk type information of general stroke patients. Herein, the analysis device compares the reference data with the information on the types of cerebral artery chunks of the subject, to evaluate whether the subject is normal, a stroke patient with ICAS, or a general stroke patient.

Furthermore, the analysis device may use another learning model that receives chunk classification information of the subject and evaluates whether the subject has a disease. In this case, the learning model must be trained in advance to receive feature values called chunk classification information of the subject and output whether or not the subject has a disease. The input chunk classification information may be information on chunk classification recognized from the entire MRA image that has a matrix form composed of images or vectors.

Furthermore, the analysis device may define characteristics (characteristic information) for a specific segment or a specific chunk composed of the corresponding spots based on features of spots capable of being extracted from the brain MRA image. It is assumed that the analysis device has extracted the features for all spots in the image. The features may be values determined based on at least one of the cerebral vessel cross-section area, maximally inscribed sphere radius, minimum and maximum diameter, maximum-minimum radius ratio, surface circumference, distortion, curvature, and luminal circularity.

The analysis device may define characteristics of a specific segment based on features of spots belonging to the segment. For example, the analysis device may determine values determined by statistical scales, such as an average, a division, a standard deviation, a skewness, and the like of the features of spots belonging to the corresponding segment, as characteristics of the corresponding segment.

In addition, the analysis device may define characteristics of a specific chunk based on features of spots belonging to the corresponding chunk. For example, the analysis device may determine values determined by statistical scales, such as an average, a division line, a standard deviation, and a skewness of the features of spots belonging to the corresponding chunk, as a characteristic of the corresponding chunk.

Furthermore, the analysis device may define characteristics of a specific chunk based on features of the segments belonging to the corresponding chunk. For example, the analysis device may determine values determined by statistical scales, such as an average, a division, a standard deviation, and a skewness of features of segments belonging to the corresponding chunk, as characteristics of the corresponding chunk.

The analysis device may define the condition of the subject based on characteristics of the segments or chunks extracted from the brain MRA image of the subject. That is, the analysis device may identify the condition of the subject based on characteristics of the segments or chunks, and provide an appropriate diagnosis and the like using the identification result.

Figure 11:
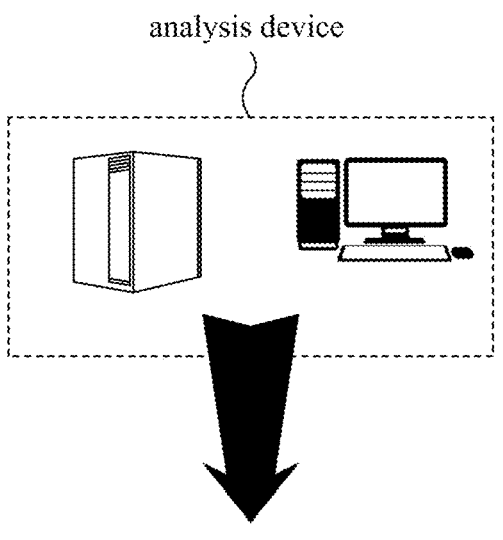
FIG. 11 illustrates an example of an analysis device for analyzing cerebral artery chunks.
Figure 11:
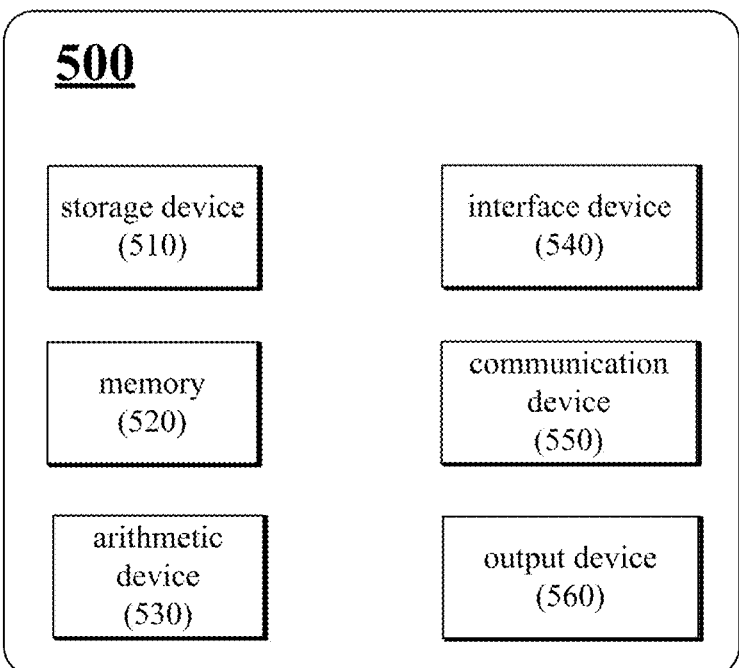

FIG. 11 illustrates an example of an analysis device 500 for analyzing a cerebral artery chunk. The analysis device 500 corresponds to the aforementioned analysis device (130 and 140 in FIG. 1). The analysis device 500 may be physically implemented in various forms. For example, the analysis device 500 may have a form of a computer device such as a PC, a network server, and a chipset dedicated to data processing.

The analysis device 500 may include a storage unit 510, a memory 520, a computing unit 530, an interface device 540, a communication device 550, and an output unit 560.

The storage unit 510 may store MRA images generated by the MRA.

The storage unit 510 may store codes or programs to extract the aforementioned cerebrovascular structure (spot, segment, etc.) from the MRA image.

The storage unit 510 may store codes or programs to extract feature values (feature vectors) for spots of a cerebrovascular structure. (i) The feature values may include at least one of factors, such as a large cerebrovascular cross-section area, a maximum inscribed sphere radius, a minimum diameter, a maximum diameter, a maximum-minimum radius ratio, a surface circumference, distortion, curvature, and lumen roundness. (ii) Furthermore, the feature values may further include a brightness value for the corresponding spot area.

The storage unit 510 may store the learning model that classifies the corresponding chunks in units of spots, as described in FIGS. 2 and 3.

The storage unit 510 may store the aforementioned reference data.

Furthermore, the storage unit 510 may store a learning model that receives chunk features of a subject and evaluates conditions of the subject of the current input image.

The memory 520 may store data and information generated during a process in which the analysis device 500 classifies cerebral artery chunks in an MRA image or identifies whether a patient has a brain disease.

The interface device 540 serves to receive certain commands and data from the outside. The interface device 540 may receive an MRA image from an input unit or an external storage unit which is physically connected. The interface device 540 may transmit, to an external object, a result obtained by classifying the MRA image.

The communication device 550 refers to a component that receives and transmits certain information through a wired or wireless network. The communication device 550 may receive the MRA image from the external object. Alternatively, the communication device 550 may transmit the result obtained by classifying the MRA image, to an external object such as a user terminal.

Since the interface device 540 and the communication device 550 are configured to send and receive certain data from a user or other physical object, they may also be referred to as an input/output unit in combination. The interface device 540 and the communication device 550 may also be referred to as an input unit in combination, when being limited to information or data input functions.

The output unit 560 serves to output certain information. The output unit 560 may output interfaces necessary for data processing, MRA images, cerebrovascular structures (4D models) extracted from MRA images, chunk classification, cerebral artery branch classification, and brain disease classification.

The computing unit 530 may classify the cerebral artery chunks in the MRA image.

The computing unit 530 may reconstruct the structures in the MRA image through geometry processing. Here, the computing unit 530 may identify spots, segments, etc., which are the cerebrovascular structures as described above.

The computing unit 530 may segment a plurality of cells based on each vertex of the isosurfaces in the continuous 3D space in the MRA image. In this process, the computing unit 530 may perform a pre-processing process, such as noise removal and normalization in an image. The computing unit 530 segments the structure into a plurality of cells constituting the vascular surface, and extracts the main arterial centerline from the border surface of each cell in cerebrovascular MRA.

The computing unit 530 may segment the vascular surface into cells of a certain size in the cerebrovascular MRA image, to extract the starting point and skeleton of the central line of the brain artery based on the vascular surface. The computing unit 530 may perform vascular skeleton refinement to make the end point of the center line more distinct. The computing unit 530 may (i) skeletonize the cerebrovascular regions and surfaces; (ii) prune branches under a predetermined threshold; (iii) create a linked list of tree structures based on the refined backbone structure; and (iv) determine the end point by designating a leaf node from the linked list. The analysis device may extract the center line of the blood vessel by tracing the cell boundary connecting the determined start point and end point.

The computing unit 530 may identify spots, which are basic units of cubic cells of a 3D cerebral artery tree having regular intervals from the center line of the artery. In addition, the computing unit 530 may identify a segment of a specific region in which a number of spots is segmented based on a branch point in the vascular structure.

The computing unit 530 may input the spots extracted from the MRA image into the learning model in units of spots to classify chunks to which the input spots belong. The computing unit 530 may extract feature values of spots and input the extracted feature value to the learning model. The operation and learning process of the learning model are described above. The learning model may be a DNN-based model.

In addition, the computing unit 530 may determine a final classification result in units of segments. As mentioned above, the computing unit 530 may set a value of the most classified results based on the chunk classification results of spots belonging to the same segment, as a result of chunk classification of spots belonging to the corresponding segment.

Through this process, a chunk to which each spot belongs may be determined, and chunk type information may be calculated from the whole cerebrovascular image.

Meanwhile, the computing unit 530 may identify whether the patient has a specific brain disease on the basis of the MRA image. Herein, the computing unit 530 should use a pre-learned model for the purpose of brain disease identification. The computing unit 530 may compute chunk type information of the subject from the MRA image of the subject by using the first learning model (chunk classification model). Thereafter, the computing unit may evaluate the condition of the subject using a value computed by inputting the chunk type information to the second learning model (subject condition classification model).

Furthermore, the computing unit 530 may define features of a specific segment or a specific chunk composed of corresponding spots based on features of spots capable of being extracted from a brain MRA image. It is assumed that the computing unit 530 extracts features of all spots in the image. The features may be values determined based on at least one element of cerebral vessel cross-section area, maximally inscribed sphere radius, minimum and maximum diameter, maximum-minimum radius ratio, surface circumference, distortion, curvature, and luminal circularity.

The computing unit 530 may define features of a specific segment based on features of spots belonging to the corresponding segment. For example, the computing unit 530 may determine values determined by a statistical scale, such as an average, a divergent line, a standard deviation, and a skewness of features of spots belonging to the corresponding segment, as features of the corresponding segment.

In addition, the computing unit 530 may define features of a specific chunk based on features of spots belonging to the corresponding chunk. For example, the computing unit 530 may determine values determined by a statistical scale, such as an average, a divergent line, a standard deviation, and a skewness of features of spots belonging to the corresponding chunk, as features of the corresponding chunk.

Furthermore, the computing unit 530 may define features of a specific chunk based on features of segments belonging to the corresponding chunk. For example, the computing unit 530 may determine values determined by a statistical scale, such as an average, a divergent line, a standard deviation, and a skewness of features of segments belonging to the corresponding chunk, as features of the corresponding chunk.

The computing unit 530 may define the condition of the subject based on features of segments or chunks extracted from the brain MRA image of the corresponding subject. That is, the computing unit 530 may identify the condition of the subject based on the features of the segments or the features of the chunks, and provide an appropriate diagnosis and the like using the identification result.

The computing unit 530 may be a device such as a processor that processes data and processes certain operations, an AP, or a chip in which program is embedded.

In addition, the image processing method, the MRA-based cerebral arterial blood vessel analysis method, the cerebral artery chunk classification method, and the brain disease chunk type based patient evaluation method as described above may be implemented as a program (or application) containing an executable algorithm capable of being executed on a computer. The program may be stored and provided in a temporary or non-transitory computer readable medium.

A non-transitory readable medium is not a medium that stores data for a short moment, such as a register, cache, or memory, but a medium that stores data semi-permanently and is capable of reading by a device. Specifically, various applications or programs described above may be stored and provided in a non-transitory readable medium, such as CD, DVD, hard disk, Blu-ray disc, USB, memory card, read-only memory (ROM), programmable read only memory (PROM), erasable PROM (EPROM) or electrically EPROM (EEPROM) or flash memory.

The temporary readable medium refers to various RAMs, such as static RAM (SRAM), dynamic RAM (DRAM), synchronous DRAM, SDRAM, double data rate SDRAM

13

(DDR SDRAM), enhanced SDRAM (ESDRAM), Synclink DRAM (SLDRAM), and Direct Rambus RAM (DRRAM)

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of analyzing a cerebrovascular image based on cerebrovascular chunk features, the method comprising:
   receiving, by an analysis device, a cerebrovascular image of a subject;
   extracting, by the analysis device, a plurality of vascular unit structures from the cerebrovascular image based on geometric features of a 3-Dimensional (3D) model;
   extracting, by the analysis device, feature values for each of the plurality of vascular unit structures;
   inputting, by the analysis device, the feature values of each of the plurality of vascular unit structures into a learning model trained in advance, classifying chunks to which each of the plurality of vascular unit structures belongs, and generating chunk features for the cerebrovascular image; and
   evaluating, by the analysis device, a condition of the subject based on the chunk features, wherein a vascular unit structure, of the vascular unit structures, is a spot, and the spot is a cell arranged at regular intervals along an artery center line extracted from the cerebrovascular image.

2. The method of claim 1, wherein the chunk is, as a higher structure of a vessel branch including at least one vessel branch type, the vascular unit structure segmented into different types according to at least one criterion of (i) symmetry; (ii) anterior or posterior; (iii) basal or pial; and (iv) a group including criteria of middle cerebral arteries (MCA), anterior cerebral arteries (ACA) and posterior cerebral arteries (PCA).

3. The method of claim 1, wherein the feature values include cerebral vessel cross-sectional area, maximum inscribed sphere radius, minimum diameter, maximum diameter, maximum-minimum radius ratio, surface circumference, distortion, curvature, and lumen roundness.

4. The method of claim 3, wherein the feature values further include a brightness value of the vascular unit structure.

5. The method of claim 1, wherein the generating of the chunk features includes:
   performing, by the analysis device, primary chunk classification for each of the plurality of vascular unit structures using the learning model; and
   performing, by the analysis device, secondary chunk classification for the vascular unit structures belonging to same segment, in a majority voting manner based on results of the primary chunk classification of the vascular unit structures belonging to the same segment among the plurality of vascular unit structures,
   wherein the segment is composed of vascular unit structures belonging to a region segmented by a branch point in a vascular structure.

6. The method of claim 1, wherein the analysis device evaluates the condition of the subject by comparing the chunk features with reference data.

7. The method of claim 1, wherein the analysis device evaluates the condition of the subject by inputting the chunk features into a separate learning model learned in advance.

8. An analysis device for analyzing a cerebrovascular image based on cerebrovascular chunk features, the device comprising:
   an input unit receiving a cerebrovascular image of a subject;
   a storage unit storing a learning model that classifies chunks to which a vascular unit structure belongs; and
   a computing unit extracting a plurality of vascular unit structures based on geometric features of a 3-Dimensional (3D) model from the cerebrovascular image, inputting feature values for each of the plurality of vascular unit structures into the learning model to classify chunks to which each of the plurality of vascular unit structures belongs and generate chunk features for the cerebrovascular image, and evaluating a condition of the subject based on the chunk features, wherein the vascular unit structure is a spot, and the spot is a cell arranged at regular intervals along an artery center line extracted from the cerebrovascular image.

9. The device of claim 8, wherein the chunk is the vascular unit structure segmented into different types according to at least one criterion of (i) symmetry; (ii) anterior or posterior; (iii) basal or pial; and (iv) a group including criteria of middle cerebral arteries (MCA), anterior cerebral arteries (ACA) and posterior cerebral arteries (PCA), as a higher structure of a vessel branch including at least one vessel branch type.

10. The device of claim 8, wherein the feature values include cerebral vessel cross-sectional area, maximum inscribed sphere radius, minimum diameter, maximum diameter, maximum-minimum radius ratio, surface circumference, distortion, curvature and lumen roundness.

11. The device of claim 10, wherein the feature values further include a brightness value of the vascular unit structure.

12. The device of claim 8, wherein the computing unit performs primary chunk classification for each of the plurality of vascular unit structures using the learning model, and performs secondary chunk classification for the vascular unit structures belonging to same segment, in a majority voting manner based on results of the primary chunk classification of the vascular unit structures belonging to the same segment among the plurality of vascular unit structures; and
   wherein the segment is composed of vascular unit structures belonging to a region segmented by a branch point in a vascular structure.

13. The device of claim 8, wherein the storage unit further stores reference data according to a phenotype; and
   the computing unit compares the reference data with the chunk features to evaluate the condition of the subject.

14. The device of claim 8, wherein the learning model is a first learning model, and wherein the storage unit further stores a second learning model that receives chunk pattern information and classifies the condition of the subject; and
the computing unit inputs the chunk features to the second learning model and evaluates the condition of the subject based on a value output.

15. A method of analyzing a cerebrovascular image based on cerebrovascular chunk features, the method comprising:
receiving, by an analysis device, a cerebrovascular image of a subject;
extracting, by the analysis device, a plurality of vascular unit structures based on geometric features of a 3-Dimensional (3D) model from the cerebrovascular image;
extracting, by the analysis device, feature values for each of the plurality of vascular unit structures;
inputting, by the analysis device, the feature values of each of the plurality of vascular unit structures into a learning model trained in advance, and classifying chunks to which each of the plurality of vascular unit structures belongs;
determining, by the analysis device, characteristic information on a plurality of chunks segmented in the cerebrovascular image based on the feature values of the vascular unit structure belonging to the chunk; and
evaluating, by the analysis device, a condition of the subject based on the characteristic information on the plurality of chunks, wherein the vascular unit structure is a spot, and the spot is a cell arranged at regular intervals along an artery center line extracted from the cerebrovascular image.

* * * * *